(12) United States Patent
Fujiwara et al.

(10) Patent No.: US 8,667,847 B2
(45) Date of Patent: Mar. 11, 2014

(54) ULTRASONIC TESTING APPARATUS FOR PIPE OR TUBE END PORTION

(75) Inventors: Kenji Fujiwara, Osaka (JP); Hiroshi Kubota, Osaka (JP); Tomoyuki Obata, Osaka (JP); Masaki Yamano, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 0 days.

(21) Appl. No.: 13/239,511

(22) Filed: Sep. 22, 2011

(65) Prior Publication Data

US 2012/0067129 A1 Mar. 22, 2012

Related U.S. Application Data

(63) Continuation of application No. PCT/JP2010/052146, filed on Feb. 15, 2010.

(30) Foreign Application Priority Data

Mar. 30, 2009 (JP) ................................. 2009-081422

(51) Int. Cl.
*G01N 29/04* (2006.01)
(52) U.S. Cl.
USPC .............................................. 73/644; 73/622
(58) Field of Classification Search
USPC .................................... 73/644, 620, 622, 623
See application file for complete search history.

(56) References Cited

U.S. PATENT DOCUMENTS

| | | | | |
|---|---|---|---|---|
| 4,246,794 A | * | 1/1981 | Sheets et al. | 73/637 |
| 4,718,277 A | * | 1/1988 | Glascock | 73/622 |
| RE34,923 E | * | 5/1995 | Ruesch | 137/15.11 |
| 5,576,492 A | * | 11/1996 | Phalin | 73/634 |
| 6,235,246 B1 | * | 5/2001 | Kao | 422/145 |
| 6,935,178 B2 | * | 8/2005 | Prause | 73/622 |

FOREIGN PATENT DOCUMENTS

| | | | |
|---|---|---|---|
| GB | 2326210 | * | 12/1998 |
| JP | 60-29278 | | 2/1985 |
| JP | 2005-207795 | | 8/2005 |
| JP | 2008-139191 | | 6/2008 |

* cited by examiner

*Primary Examiner* — J M Saint Surin
(74) *Attorney, Agent, or Firm* — Clark & Brody

(57) ABSTRACT

An ultrasonic testing apparatus for a pipe end portion, which enables accurate ultrasonic testing, comprises an ultrasonic probe disposed under the pipe end portion. The probe 1 transmits ultrasonic waves to the pipe end portion and receives the ultrasonic waves therefrom. A probe holder houses the probe which is disposed under the pipe end portion to face the pipe end portion and follows the pipe rotation. The probe holder comprises a coupling medium reserver part that surrounds a space between the probe and the pipe end portion to contain a coupling medium therein and comprises a coupling medium reserver part body into which the coupling medium is supplied. An annular bellows part, which communicates with the reserver part body, can expand and contract vertically and an annular spacer, which is attached to the upper side of the bellows part and an upper surface thereof has a flat horizontal surface.

3 Claims, 4 Drawing Sheets

SUPPORT  SUPPORT

T  1  W

P  T  W  1

ULTRASONIC TESTING APPARATUS FOR PIPE OR TUBE END PORTION

TECHNICAL FIELD

The present invention relates to an apparatus for ultrasonic testing of an end portion of a pipe or tube such as a steel pipe or tube. More particularly, the present invention relates to an ultrasonic testing apparatus for a pipe or tube end portion, which enables accurate ultrasonic testing by the stable interposition of a coupling medium between the pipe or tube (hereinafter referred to as "pipe" when deemed appropriate) end portion and an ultrasonic probe.

BACKGROUND ART

An ultrasonic testing method has been employed widely as a nondestructive inspection method for a pipe such as a steel pipe. In the ultrasonic testing method, a coupling medium such as water is interposed between the pipe and an ultrasonic probe, ultrasonic waves transmitted from the ultrasonic probe are applied to the pipe, and the ultrasonic waves reflected by the pipe are received by the ultrasonic probe.

As an ultrasonic testing method in which ultrasonic probe is disposed under a pipe laid in the horizontal direction, there is a publicly known method for ultrasonic testing of a pipe P in which, as shown in FIG. 1, while an ultrasonic probe 1 is immersed in water W stored in a water tank T, the lower surface of the pipe P is immersed partially in the water W, and the pipe P is conveyed in the axial direction thereof and is rotated in the circumferential direction thereof (for example, refer to "Ultrasonic Testing Series (III) Ultrasonic Testing Method for Seamless Steel Pipe" from the Iron and Steel Institute of Japan, Apr. 15, 1988, pp. 95-96).

According to the above-described method, since the water W serving as a coupling medium can be interposed stably between the pipe P and the ultrasonic probe 1, accurate ultrasonic testing can be performed.

In the configuration shown in FIG. 1, unfortunately, the pipe P is supported at least at two points outside the water tank T. The problem, therefore, is that ultrasonic testing cannot be performed on a pipe end portion, where such a two-point support cannot be used, within the water W in the water tank T. Therefore, the configuration shown in FIG. 1 is mainly used in ultrasonic testing of the central portion of pipe except the pipe end portions.

On the other hand, as an ultrasonic testing apparatus for a pipe end portion, there is a publicly known apparatus provided with an ultrasonic probe and a follow-up device, which causes the ultrasonic probe to follow the pipe rotating in the circumferential direction (for example, refer to JP2008-139191A).

In the case where the ultrasonic probe for ultrasonic testing of the pipe end portion is disposed over the pipe laid in the horizontal direction, it is conceivable for example to use a structure that causes coupling medium to flow down between the ultrasonic probe and the pipe end portion. However, the same structure cannot be used in the case where the ultrasonic probe is disposed under the pipe. In the case where the ultrasonic probe for ultrasonic testing of the pipe end portion is disposed under the pipe, it is conceivable for example to use the water tank as shown in FIG. 1 and immerse the support structure and the follow-up device for the pipe into water in the water tank in a certain configuration. Unfortunately, such a configuration may not be practical because it may be complicated and require a strong waterproof structure, which leads to poor maintainability and an increased cost.

DISCLOSURE OF THE INVENTION

The present invention has been made in view of the above-described conventional art, and accordingly an object thereof is to provide an ultrasonic testing apparatus for a pipe end portion, which enables accurate ultrasonic testing by the stable interposition of a coupling medium between the pipe end portion and an ultrasonic probe.

In order to achieve the object, the ultrasonic testing apparatus in accordance with the present invention comprises: an ultrasonic probe which is disposed under the end portion of a pipe or tube laid in the horizontal direction to face the pipe or tube end portion, the ultrasonic probe transmitting ultrasonic waves to the end portion of the pipe or tube and receiving the ultrasonic waves therefrom; and a probe holder housing the ultrasonic probe which is disposed under the end portion of the pipe or tube to face the pipe or tube end portion and follows the pipe or tube rotating in the circumferential direction. The probe holder comprises a coupling medium reserver part which surrounds a space between the ultrasonic probe and the end portion of the pipe or tube to contain a coupling medium therein. The coupling medium reserver part comprises: a coupling medium reserver part body into which the coupling medium is supplied; an annular bellows part which is attached to the upper side of the coupling medium reserver part body so as to internally communicate with the coupling medium reserver part body, and can expand and contract vertically; and an annular spacer which is attached to the upper side of the bellows part, and at least the upper surface of the annular spacer is a flat horizontal surface.

According to the ultrasonic testing apparatus in accordance with the present invention, the probe holder housing the ultrasonic probe that is disposed under the pipe or tube end portion to face the pipe or tube end portion includes the coupling medium reserver part that surrounds the space between the ultrasonic probe and the pipe or tube end portion to contain the coupling medium therein. When the coupling medium is supplied to the coupling medium reserver part body included in the coupling medium reserver part, the coupling medium flows into the annular bellows part internally communicating with the coupling medium reserver part body. The coupling medium flowing into the bellows part goes to the annular spacer attached to the bellows part and comes into contact with the pipe or tube end portion.

Since at least the upper surface of the annular spacer is a flat horizontal surface, by properly adjusting the flow rate of the coupling medium supplied to the coupling medium reserver part body, a film is formed by the coupling medium raised beyond the upper surface of the spacer by the surface tension of the coupling medium. With the film of the coupling medium in contact with the pipe or tube end portion, ultrasonic waves transmitted from the ultrasonic probe are applied to the pipe or tube end portion via the coupling medium in the coupling medium reserver part body, the coupling medium in the bellows part, and the film. The ultrasonic waves reflected by the pipe or tube end portion are received by the ultrasonic probe via the film, the coupling medium in the bellows part, and the coupling medium in the coupling medium reserver part body.

The probe holder follows the pipe or tube rotating in the circumferential direction (i.e. the probe holder is controlled to maintain the vertical and horizontal positional relationship between the probe holder and the pipe or tube). Further, the bellows part expands and contracts vertically. Therefore, even if the pipe or tube bends or has a cross section that is not a complete round, the film of the coupling medium remains in contact with the pipe or tube end portion, and the fluctuation of the film may be suppressed. Therefore, the coupling medium is interposed stably between the pipe or tube end portion and the ultrasonic probe. Thereby, accurate ultrasonic testing can be performed.

Preferably, the coupling medium reserver part further comprises a tubular member which is attached to the lower surface of the spacer and is fitted in the bellows part.

According to the above-described preferable configuration, air bubbles in the coupling medium that may be trapped in the bellows part (especially in the folded part of the bellows part) do not reach the folded part of the bellows part, and easily rise along the inner surface of the tubular member. If the coupling medium reserver part does not have the tubular member, the air bubbles trapped in the folded part of the bellows part may gather and rise as a mass at once. In this case, the ultrasonic waves are scattered by the mass of the rising air bubbles, so that the testing accuracy may be decreased. However, when the coupling medium reserver part is provided with the tubular member as in the above-described preferable configuration, the air bubbles in the coupling medium easily rise one after another along the inner surface of the tubular member before the air bubbles gather to form a mass. Therefore, the avoidance of the decrease in testing accuracy can be expected.

Preferably, the coupling medium reserver part body is provided with a coupling medium supply port for supplying the coupling medium in the tangential direction of a predetermined arc around the vertical center axis, and a coupling medium discharge port for discharging the coupling medium in the tangential direction of the arc.

According to the above-described preferable configuration, since the coupling medium is supplied in the tangential direction of a predetermined arc around the vertical center axis through the coupling medium supply port, an eddy current of the coupling medium is produced in the coupling medium reserver part body. By this eddy current, a contamination (for example, for a steel pipe or tube, droppings of scale adhering to the steel pipe or tube surface) that may be contained in the coupling medium is carried to the coupling medium discharge port and is discharged to the outside. Therefore, the coupling medium reserver part body, and in turn the whole of the coupling medium reserver part and the ultrasonic probe can be cleaned during testing, which offers an advantage of enhanced maintainability. The eddy current also offers an advantage that air bubbles that may exert an influence on the testing accuracy are less liable to adhere to the surface of the ultrasonic probe.

According to the ultrasonic testing apparatus for a pipe or tube end portion in accordance with the present invention, accurate ultrasonic testing can be performed by the stable interposition of the coupling medium between the pipe or tube end portion and the ultrasonic probe.

BEST MODE FOR CARRYING OUT THE INVENTION

One embodiment of the present invention will now be described with reference to the accompanying drawings.

Figure 1A:
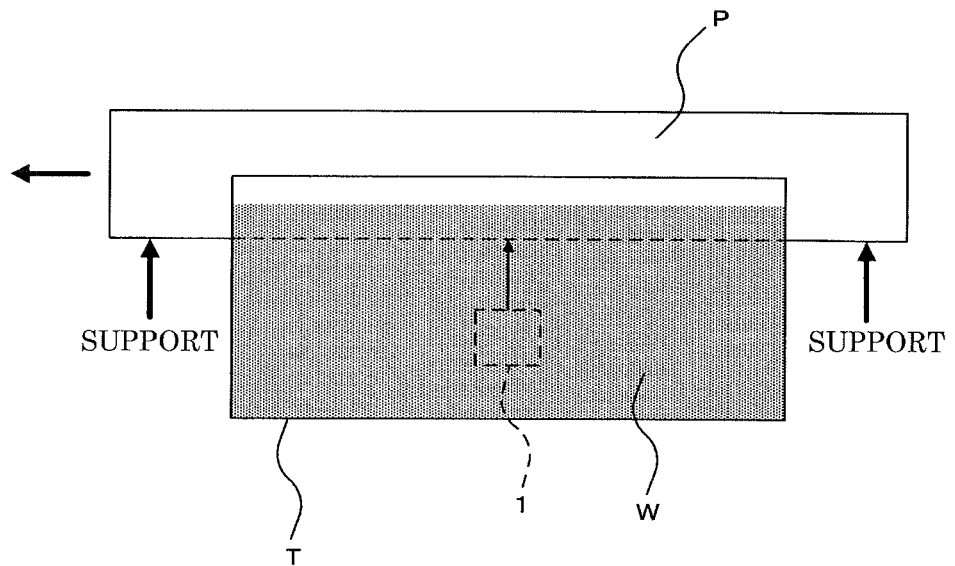
FIGS. 1 (FIG. 1A and FIG. 1B) are schematic views showing a configuration of an apparatus used in ultrasonic testing of a pipe central portion, FIG. 1A being a side view, and FIG. 1B being sectional view as viewed from the front.
Figure 1B:
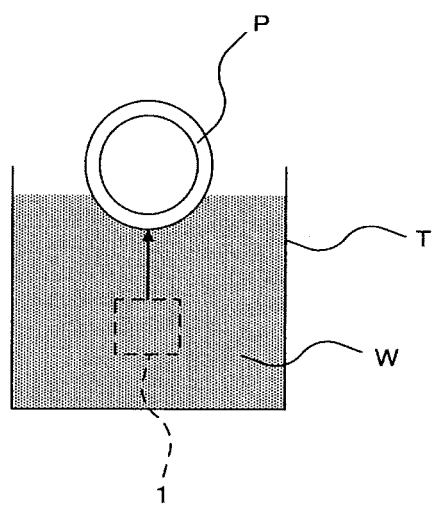
Figure 2:
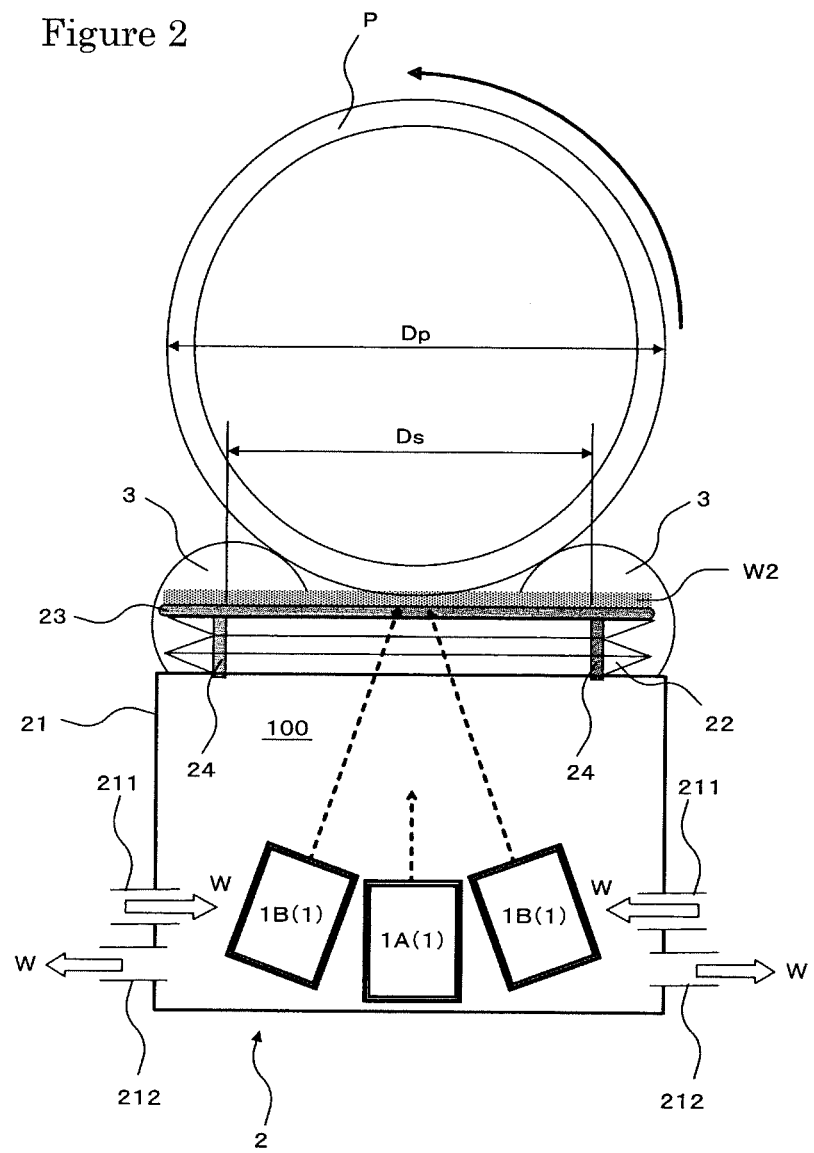
FIG. 2 is a sectional view, as viewed from the front, of an ultrasonic testing apparatus in accordance with one embodiment of the present invention.
Figure 3:
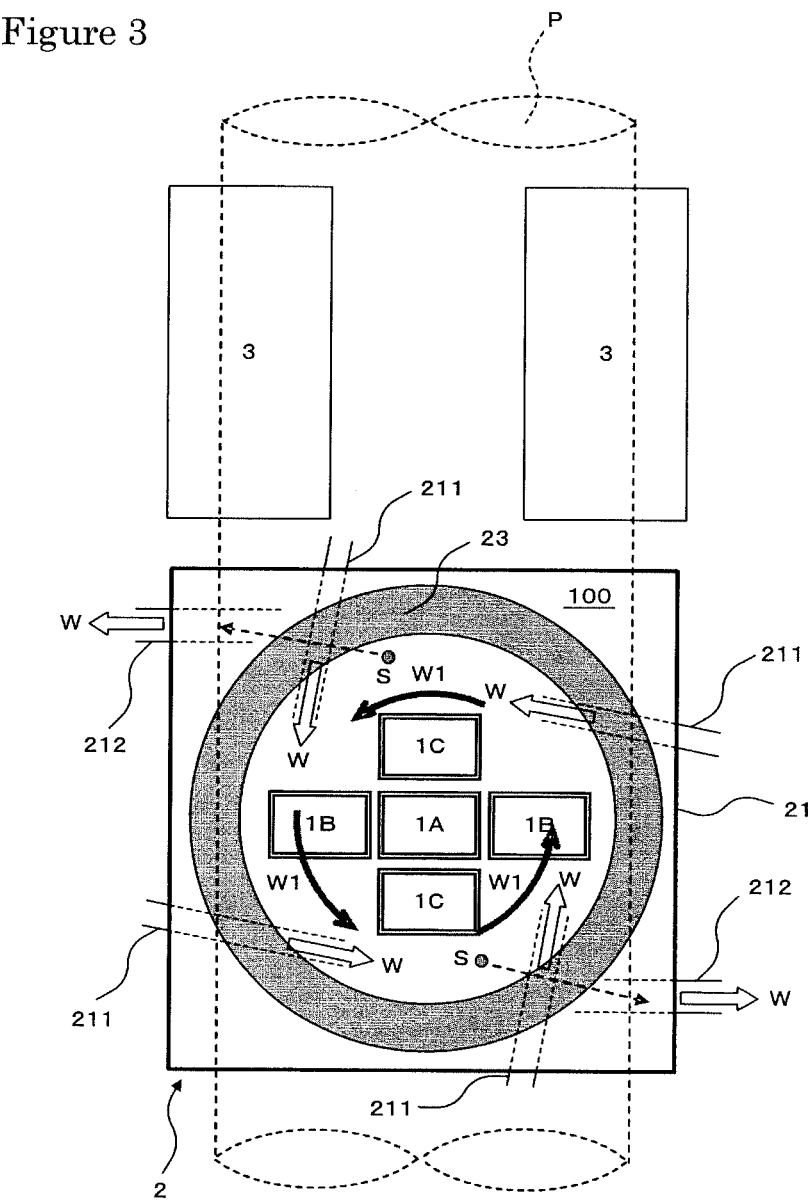
FIG. 3 is a plan view of the ultrasonic testing apparatus shown in FIG. 2.

FIG. 2 is a sectional view, as viewed from the front, of an ultrasonic testing apparatus in accordance with one embodiment of the present invention. FIG. 3 is a plan view of the ultrasonic testing apparatus shown in FIG. 2.

As shown in FIG. 2 or FIG. 3, the ultrasonic testing apparatus 100 of this embodiment comprises an ultrasonic probe 1 which is disposed under the end portion of a pipe P laid in the horizontal direction to face the pipe P end portion, the ultrasonic probe 1 transmitting ultrasonic waves to the end portion of the pipe P and receiving the ultrasonic waves therefrom; and a probe holder 2 housing the ultrasonic probe 1 which is disposed under the end portion of the pipe P to face the pipe P end portion and follows the pipe P rotating in the circumferential direction.

The pipe P is placed on turning rollers 3, so that the pipe P is rotated in the circumferential direction thereof by the rotation of the turning rollers 3. The probe holder 2 is disposed under the end portion of the pipe P projecting from the turning rollers 3 to face the pipe end portion.

The ultrasonic testing apparatus 100 of this embodiment is provided with an ultrasonic probe 1A, ultrasonic probes 1B (two probes), and ultrasonic probes 1C (two probes), all of which constitute the ultrasonic probe 1. The ultrasonic probe 1A is used to detect lamination (a planar flaw parallel to the inner and outer surfaces of the pipe P) by propagating ultrasonic waves in the wall thickness direction of the pipe P. The ultrasonic probes 1B are inclined in the circumferential direction of the pipe P, and are used to detect an axial flaw (a flaw extending in the axial direction of the pipe P) by propagating ultrasonic waves in the circumferential direction of the pipe P. The ultrasonic probes 1C are inclined in the axial direction of the pipe P, and are used to detect a circumferential flaw (a flaw extending in the circumferential direction of the pipe P) by propagating ultrasonic waves in the axial direction of the pipe P. These ultrasonic probes 1A to 1C are positioned so that the incident points of the transmitted ultrasonic waves to the pipe P coincide substantially with each other.

The probe holder 2 of this embodiment is, as described above, configured to follow the pipe P rotating in the circumferential direction. Specifically, the probe holder 2 is attached to a follow-up device (not shown). This follow-up device moves the probe holder 2 vertically and horizontally to maintain the vertical and horizontal positional relationship between the probe holder 2 and the pipe P (thereby, also maintaining the positional relationship between the ultrasonic probe 1 housed in the probe holder 2 and the pipe P) on the basis of a measurement result of displacement of the outer surface of the rotating pipe P. Although the above-described follow-up device is not subject to any special restriction and various publicly known follow-up devices can be employed, the follow-up device described in, for example, JP2008-139191A is preferably employed.

The probe holder 2 includes a coupling medium reserver part that surrounds a space between the ultrasonic probe 1 and the end portion of the pipe P to contain a coupling medium W such as water therein. In this embodiment, since the whole of the probe holder 2 functions as the coupling medium reserver part, in the explanation below, the same reference numeral as that of the probe holder 2 is applied to the coupling medium reserver part.

The coupling medium reserver part 2 includes a coupling medium reserver part body 21, an annular (in this embodiment, ring-shaped) bellows part 22, and an annular (in this embodiment, ring-shaped) spacer 23. Also, the coupling medium reserver part 2 of this embodiment includes a tubular (in this embodiment, cylindrical) member 24 as a preferable configuration.

The coupling medium reserver part body 21 of this embodiment includes coupling medium supply ports 211 (in this embodiment, four ports) and coupling medium discharge ports 212 (in this embodiment, two ports). Into and from the coupling medium reserver part body 21, the coupling medium W is supplied through the coupling medium supply ports 211, and the coupling medium W is discharged through the coupling medium discharge ports 212. The flow rate of the coupling medium W supplied through the coupling medium supply ports 211 (the total flow rate supplied through the four coupling medium supply ports 211) is set higher than the flow rate of the coupling medium W discharged through the coupling medium discharge ports 212 (the total flow rate discharged through the two coupling medium discharge ports 212). For example, the flow rate of the coupling medium W discharged through the coupling medium discharge ports 212 is set at about 10 to 15% of the flow rate of the coupling medium W supplied through the coupling medium supply ports 211. Therefore, the coupling medium W stays in the coupling medium reserver part body 21.

In this embodiment, as a preferable configuration, the coupling medium supply ports 211 are arranged so that the coupling medium W is supplied in the tangential direction of a predetermined arc around the vertical center axis. Specifically, the coupling medium supply ports 211 extend in the tangential direction of the aforementioned arc. Also, the coupling medium discharge ports 212 are arranged so that the coupling medium W is discharged in the tangential direction of the aforementioned arc. Specifically, the coupling medium discharge ports 212 extend in the tangential direction of the aforementioned arc. Since the coupling medium W is supplied in the tangential direction of the aforementioned arc through the coupling medium supply ports 211, an eddy current W1 of the coupling medium W is produced in the coupling medium reserver part body 21. By this eddy current W1, a contamination (for example, for a steel pipe P, droppings of scale S adhering to the steel pipe surface) that may be contained in the coupling medium W is carried to the coupling medium discharge ports 212 and is discharged to the outside. Therefore, the coupling medium reserver part body 21, and in turn the whole of the coupling medium reserver part 2 and the ultrasonic probe 1 can be cleaned during testing, which offers an advantage of enhanced maintainability. The eddy current W1 also offers an advantage that air bubbles that may exert an influence on the testing accuracy are less liable to adhere to the surface of the ultrasonic probe 1.

The flow rate of the coupling medium W supplied through the coupling medium supply ports 211 is preferably adjusted to about 2 to 6 liters/minute. At this time, the flow rate of the coupling medium W discharged through the coupling medium discharge ports 212 is about 10 to 15% of the supply flow rate, being lower than 1 liter/minute. If the flow rate of the coupling medium W is lower than 2 liters/minute, the shortage of flow rate makes it difficult to form a film W2 that is formed by the coupling medium W rising beyond the upper surface of the spacer 23. Also, if the flow rate of the coupling medium W is higher than 6 liters/minute, the excess flow rate raises the possibility that the film W2 of the coupling medium rising beyond the upper surface of the spacer 23 may fall into disorder. The flow rate of the coupling medium W supplied through the coupling medium supply ports 211 is set in the above-described range, and as described later, an inside diameter Ds of the spacer 23 is set at 25% or more of an outside diameter Dp of the pipe P, whereby the thickness of the film W2 of the coupling medium can be controlled to about 2 to 3 mm.

The bellows part 22 of this embodiment is attached to the upper side of the coupling medium reserver part body 21 so as to internally communicate with the coupling medium reserver part body 21, and can expand and contract vertically. Specifically, an opening (in this embodiment, a circular opening) is formed in the upper surface of the coupling medium reserver part body 21, and the annular bellows part 22 is installed so as to surround this opening. The innermost diameter of the bellows part 22 is set approximately equal to (equal to or slightly smaller than) the diameter of the opening.

The material for forming the bellows part 22 is not subject to any special restriction. However, a material having high wear resistance and expandability is preferably used. High wear resistance is useful for suppressing a breakage in the folded part of the bellows part 22 caused by repeated expansion and contraction of the bellows part 22. High expandability is useful for suppressing the fluctuation of the film W2 due to the direct transmission of an impact caused by the contact of the pipe P with the spacer 23 to the film W2 of the coupling medium. As a material for forming the bellows part 22, silicone rubber is preferably used because of its high wear resistance and expandability.

The spacer 23 of this embodiment is attached to the upper side of the bellows part 22, and at least the upper surface of the spacer (in this embodiment, the lower surface thereof, too) is a flat horizontal surface. Also, the tubular member 24 of this embodiment is attached to the lower surface of the spacer 23, and is fitted in the bellows part 22. Specifically, the outside diameter of the tubular member 24 is set approximately equal to (equal to or slightly smaller than) the innermost diameter of the bellows part 22 so that the tubular member 24 is fitted in the bellows part 22. Thereby, the outside diameter of the tubular member 24 is set approximately equal to (equal to or slightly smaller than) the diameter of the opening formed in the upper surface of the coupling medium reserver part body 21. Therefore, when the spacer 23 attached to the bellows part 22 is lowered by the contraction of the bellows part 22 and accordingly the tubular member 24 is also lowered, the lower end portion of the tubular member 24 passes through the opening in the coupling medium reserver part body 21 and is inserted into the coupling medium reserver part body 21. The spacer 23 is preferably formed of a stainless steel having high wear resistance because the frequency of contact of the spacer 23 with the end portion of the steel pipe P is high. Further preferably, the spacer 23 and the tubular member 24 are formed integrally of a stainless steel.

As a method for attaching the spacer 23 to the bellows part 22, a method may be employed in which the spacer 23 is directly fixed to the upper portion of the bellows part 22 using machine screws or the like. However, the spacer 23 of this embodiment is mounted with the tubular member 24, and the tubular member 24 is fitted in the bellows part 22. Therefore, even if the spacer 23 is not fixed directly to the bellows part 22, the spacer 23 is attached to the bellows part 22 via the tubular member 24 in a state of being relatively stable.

Figure 4:
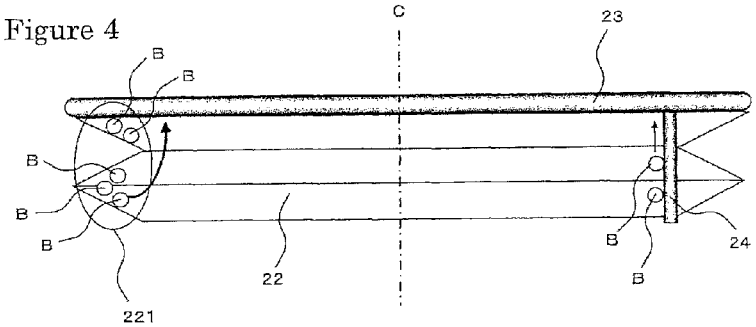
FIG. 4 is a sectional view, as viewed from the front, for explaining the operation of a tubular member shown in FIG. 2.

FIG. 4 is a sectional view, as viewed from the front, for explaining the operation of the tubular member 24 of this embodiment. In FIG. 4, the left-hand side of a dashed line C shows a state in which the tubular member 24 is not provided, and the right-hand side thereof shows a state in which the tubular member 24 is provided. As shown in FIG. 4, since the coupling medium reserver part 2 of this embodiment is provided with the tubular member 24, air bubbles B in the coupling medium W do not reach a folded part 221 of the bellows part 22, and easily rise along the inner surface of the tubular member 24. If the coupling medium reserver part 2 does not have the tubular member 24, the air bubbles B trapped in the folded part 221 of the bellows part 22 may gather and rise as a mass at once. In this case, the ultrasonic waves are scattered by the mass of the rising air bubbles B, so that the testing accuracy may be decreased. In contrast, when the coupling medium reserver part 2 is provided with the tubular member 24, the air bubbles B in the coupling medium W easily rise one after another along the inner surface of the tubular member 24 before the air bubbles B gather to form a mass. Therefore, the avoidance of the decrease in testing accuracy can be expected.

The inside diameter Ds of the spacer 23 shown in FIG. 2 is preferably set at 25% or more of the outside diameter Dp of the pipe P. If the inside diameter Ds of the spacer 23 is too small as compared with the outside diameter Dp of the pipe P (less than 25%), the opening of the spacer 23 is easily closed by the outer surface of the pipe P (a state close to the state in which the outer surface of the pipe P is in surface contact with the opening of the spacer 23 is formed), and therefore the possibility that the film of the coupling medium W2 may fall into disorder rises. If the inside diameter Ds of the spacer 23 is too large, the size of the probe holder (coupling medium reserver part) 2 increases accordingly, so that the weight of the whole of the probe holder 2 including the weight of the coupling medium W staying in the probe holder 2 increases, whereby the follow-up performance of the probe holder 2 may be deteriorated. Therefore, attention must be paid to the fact that the inside diameter Ds of the spacer 23 should not be set excessively large.

In the ultrasonic testing apparatus 100 of this embodiment, which has been explained above, when the coupling medium W is supplied to the coupling medium reserver part body 21, the coupling medium W flows into the bellows part 22 internally communicating with the coupling medium reserver part body 21. The coupling medium W flowing into the bellows part 22 goes to the spacer 23 attached to the bellows part 22 and comes into contact with the end portion of the pipe P.

Since at least the upper surface of the spacer 23 is a flat horizontal surface, by adjusting the flow rate of the coupling medium W supplied to the coupling medium reserver part body 21 to a proper range as described above, the film W2 is formed by the coupling medium W raised beyond the upper surface of the spacer 23 by the surface tension of the coupling medium W. With the film W2 of the coupling medium in contact with the end portion of the pipe P, ultrasonic waves transmitted from the ultrasonic probe 1 are applied to the end portion of the pipe P via the coupling medium W in the coupling medium reserver part body 21, the coupling medium W in the bellows part 22, and the film W2. The ultrasonic waves reflected by the end portion of the pipe P are received by the ultrasonic probe 1 via the film W2, the coupling medium W in the bellows part 22, and the coupling medium W in the coupling medium reserver part body 21.

The probe holder 2 follows the pipe P rotating in the circumferential direction. Further, the bellows part 22 expands and contracts vertically. Therefore, even if the pipe P bends or has a cross section that is not a complete round, the film W2 of the coupling medium remains in contact with the end portion of the pipe P, and the fluctuation of the film may be suppressed. Therefore, the coupling medium W (including the film W2) is interposed stably between the end portion of the pipe P and the ultrasonic probe 1. Thereby, accurate ultrasonic testing can be performed.

Figure 5A:
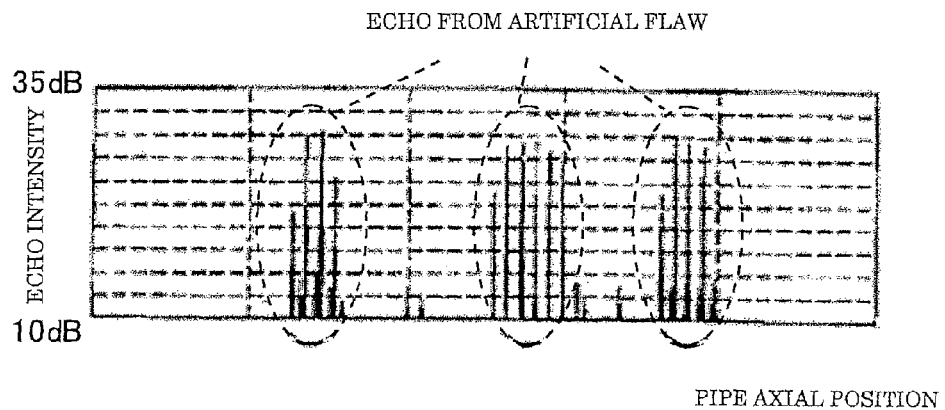
FIGS. 5 (FIG. 5A and FIG. 5B) are views showing one example of detection results of artificial flaws formed in a pipe end portion, FIG. 5A being a flaw detection chart obtained by an ultrasonic probe for detecting axial flaws, and FIG. 5B being a schematic view showing the artificial flaws.
Figure 5B:
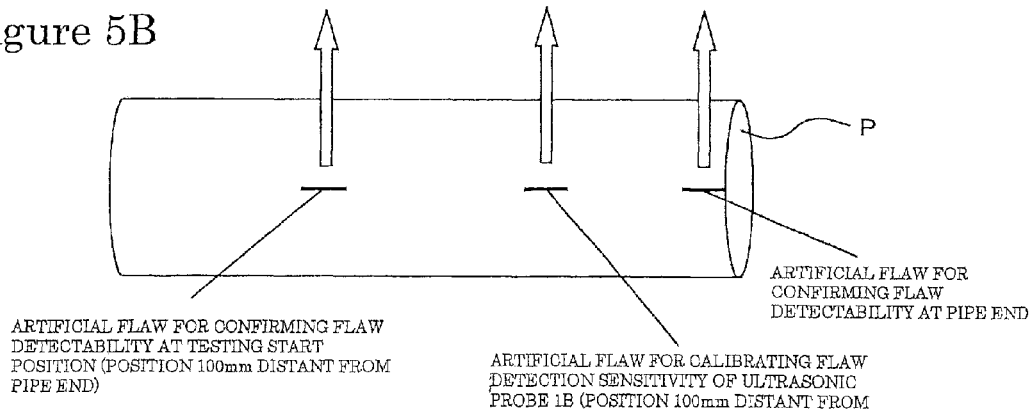

FIG. 5 are views showing one example of results of detection of artificial flaws (axial flaws) formed on the outer surface in the end portion of pipe P, which is made under the following conditions (1) to (6) by using the ultrasonic testing apparatus 100 of this embodiment. FIG. 5A is a flaw detection chart obtained by the ultrasonic probes 1B for detecting axial flaws, and FIG. 5B is a schematic view showing the artificial flaws. The abscissas of FIG. 5A represent the axial position of the pipe P, and the ordinates thereof represent echo intensity.

(1) Outside diameter of pipe P: 168 mm
(2) Rotational speed of pipe P: 113 rpm
(3) Travel speed in pipe axial direction of probe holder 2: 15.1 mm/sec
(4) Inside diameter Ds of spacer 23: 63 mm
(5) Flow rate of coupling medium (water) supplied: 5.5 liters/min
(6) Flow rate of coupling medium (water) discharged: less than 1 liter/min As can be seen from FIG. 5A, according to the ultrasonic testing apparatus 100 of this embodiment, the coupling medium can be interposed stably between the pipe end portion and the ultrasonic probe, and the artificial flaws can be detected with high accuracy. FIG. 5 shows the detection results of axial flaws only. However, it was able to confirm that in the case where circumferential flaws are formed as artificial flaws and testing is performed, the flaws can be detected with high accuracy by using the ultrasonic probes 1C, and in the case where a flat-bottomed holes are formed as artificial flaws and testing is performed, the flaws can be detected with high accuracy by using the ultrasonic probe 1A.

The invention claimed is:

1. An ultrasonic testing apparatus for a pipe or tube end portion, comprising:
   an ultrasonic probe which is disposed under the end portion of a pipe or tube laid in the horizontal direction to face the pipe or tube end portion, the ultrasonic probe transmitting ultrasonic waves to the end portion of the pipe or tube and receiving the ultrasonic waves therefrom; and
   a probe holder housing the ultrasonic probe which is disposed under the end portion of the pipe or tube to face the pipe or tube end portion and follows the pipe or tube rotating in the circumferential direction,
   the probe holder comprising a coupling medium reserver part which surrounds a space between the ultrasonic probe and the end portion of the pipe or tube to contain a coupling medium therein, and
   the coupling medium reserver part comprising:
   a coupling medium reserver part body into which the coupling medium is supplied;
   an annular bellows part which is concentrically attached to the upper side of the coupling medium reserver part body so as to internally communicate with the coupling medium reserver part body, and can expand and contract vertically; and
   an annular spacer which is concentrically attached to the upper side of the bellows part, and at least the upper surface of the annular spacer is a flat horizontal surface.

2. The ultrasonic testing apparatus for a pipe or tube end portion according to claim 1, wherein the coupling medium reserver part further comprises a tubular member which is attached to the lower surface of the spacer and is fitted in the bellows part.

3. The ultrasonic testing apparatus for a pipe or tube end portion according to claim 1, wherein the coupling medium reserver part body is provided with a coupling medium supply port for supplying the coupling medium in the tangential direction of a predetermined arc around the vertical center axis, and a coupling medium discharge port for discharging the coupling medium in the tangential direction of the arc.

* * * * *